United States Patent [19]

Hofmann

[11] Patent Number: 4,578,168

[45] Date of Patent: Mar. 25, 1986

[54] APPARATUS FOR FUSING LIVE CELLS WITH ELECTRIC FIELDS

[75] Inventor: Gunter A. Hofmann, San Diego, Calif.

[73] Assignee: Biotronics, San Diego, Calif.

[21] Appl. No.: 635,009

[22] Filed: Jul. 27, 1984

[51] Int. Cl.[4] ............................................. G01N 27/28
[52] U.S. Cl. ............................ 204/299 R; 204/183.1; 204/302; 204/272
[58] Field of Search ............... 204/272, 180 R, 299 R, 204/302, 183.1

[56] References Cited

U.S. PATENT DOCUMENTS

| | | | |
|---|---|---|---|
| 3,457,152 | 7/1969 | Maloney, Jr. et al. | 204/272 |
| 3,530,051 | 9/1970 | Ueda et al. | 204/272 |
| 3,984,303 | 10/1976 | Peters et al. | 204/272 |
| 4,269,690 | 5/1981 | Graham, III | 204/272 |
| 4,441,972 | 4/1984 | Pohl | 204/180 R |

OTHER PUBLICATIONS

Zimmermann, U., et al, "Electric Field-Induced Cell-to-Cell Fusion", *Journal of Membrane Biology*, vol. 67, pp. 165–182, (1982).

Primary Examiner—John F. Niebling
Assistant Examiner—B. J. Boggs, Jr.
Attorney, Agent, or Firm—Baker, Maxham, Callan & Jester

[57] ABSTRACT

A single wire electrode is supported at one end by a cylinder cap which has pins for guiding the electrode into an upwardly opening fusion chamber defined by a heavy metal cylinder. In a second embodiment, multiple secondary wire electrodes are spaced circumferentially about a central primary wire electrode. In a third embodiment, a laminate wire mesh electrode assembly is mounted within a rectangular cartridge fusion chamber.

13 Claims, 9 Drawing Figures

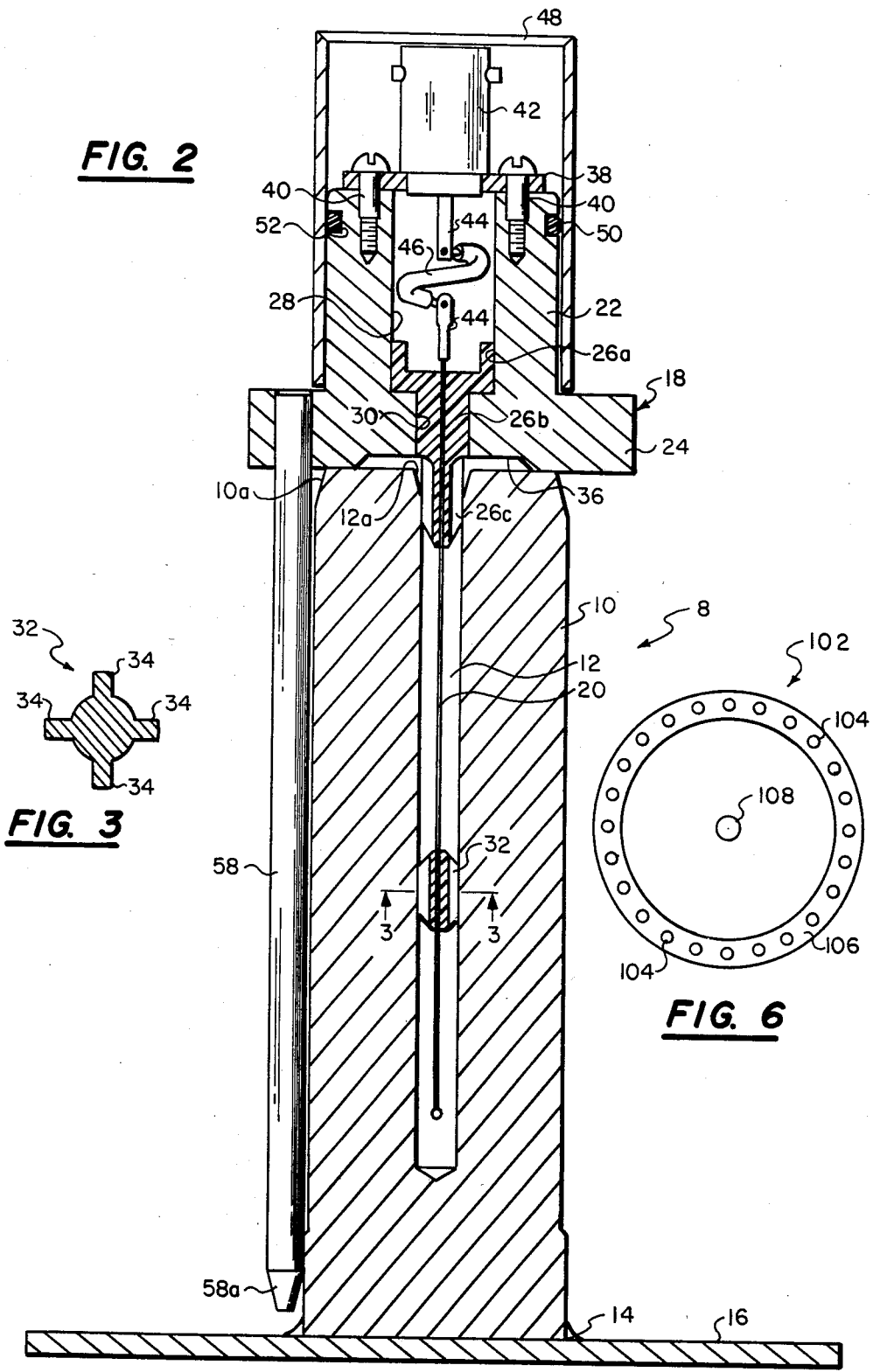

APPARATUS FOR FUSING LIVE CELLS WITH ELECTRIC FIELDS

BACKGROUND OF THE INVENTION

The present invention relates to biological engineering, and more particularly, to apparatus for performing electro cell fusion on a large scale basis.

The electro cell fusion process is generally done in several phases. In the first phase, the cells are brought close to each other to form pearl chains by exposing the cells to an alternating electric field. In the second phase, the cells which are in contact with each other are exposed for a brief moment to an alternating field of higher amplitude than the initial alternating electric field. The cells are pushed against each other and flatten out in the area of contact. In the third phase, cell fusion is initiated by one or more short, unidirectional pulses of high voltage. Under the correct conditions, pores in the cell membranes will open up and adjacent cells will fuse with each other. The resulting hybrid cell contains the genetic information of both the original cells. If the voltage is too high or the pulses too long, cell damage can occur and a non-viable hybrid results. There are particular parameters for optimal fusion yield for different cell types. In the fourth phase, the alignment alternating electric field is reapplied to maintain mechanical confinement and to aid in rounding off the fused cells.

Two physical processes are involved in the four phases of electro cell fusion. Dielectrophoresis governs the movement of the cells, i.e. alignment, compression and post fusion. Dielectric breakdown governs the actual fusion event.

Heretofore, electro cell fusion has been performed on a small scale utilizing an apparatus consisting of wires or thin metal plates on a microscope slide. A droplet of a fluid containing the live cells in suspension is deposited on this type of apparatus so that it bridges the two wires or metal plates. Suitable electric currents are then applied to the wires or plates. The droplet of cell suspension fluid is held in position by capillary action and surface tension. The volume of fluid which can be treated with such a device is typically on the order of one micro-liter. Examples of microscope slide type electro cell fusion devices are commercially available from GCA Corporation of Chicago, Ill. and D.E.P. Systems, Inc. of Metamora, Miss.

Another prior electro cell fusion device maintains the cell suspension fluid in a closed loop to permit repetitive sterile injection of fresh cells, with fused cells exiting the opposite end. One such device is available from D.E.P. Systems, Inc. and another such device is illustrated in FIG. 6 of U.S. Pat. No. 4,441,972.

It would be desirable to provide an apparatus for performing electro cell fusion on much larger fluid volumes, containing much larger number of cells to be fused, than has been possible with prior such devices. Such a large volume cell fusion apparatus would permit large scale production of hybrid cells for manufacturing monoclonal antibodies, among other uses.

U.S. Pat. No. 4,441,972 referred to above also discloses a cell sorting/electro cell fusion apparatus which is supposed to handle a large number of cells. It includes a very flat disk-shaped chamber defined between upper and lower electrode plates. The lower electrode has a plurality of concentric V-shaped grooves cut in in its upper surface. A cell suspension fluid inlet extends through the center of the lower electrode and an outlet extends through the periphery of the lower electrode. This apparatus depends upon surface effects of the grooved electrode in performing electro cell fusion. The mechanical structure is complex and requires precise parallel alignment of the electrode plates. It is not feasible to produce large volumes of viable hybrid cells with this device.

SUMMARY OF THE INVENTION

Accordingly, it is the primary object of the present invention to provide an apparatus for performing electro cell fusion in a large fluid volume.

It is another object of the present invention to provide such an apparatus which is durable and adapted for repeated use and sterilization.

Still another object of the present invention is to provide a large volume electro cell fusion apparatus in the form of a lightweight, inexpensive cartridge.

In a first embodiment of my invention, a hollow, vertical stainless steel cylinder with substantial thermal inertia defines a cell fusion chamber having a volume of approximately one milliliter. A single wire electrode supported at one end by a cylinder cap may be inserted into the cylinder so that it extends axially through the center thereof. The cap has three equally spaced guide pins which extend downwardly from the periphery of the cylinder cap and prevent the wire electrode from being bent during insertion into the cell fusion chamber. A coaxial connector on the cylinder cap permits electrical connections to the wire electrode and cylinder. The coaxial cable is connected to a signal generator which provides electrical signals with the proper waveform to accomplish the electro cell fusion process.

In a second alternate embodiment of the invention, multiple secondary wire electrodes are spaced circumferentially about a central primary wire electrode. The assembly of primary and secondary wire electrodes is supported within a cylindrical cell fusion chamber.

In a third embodiment of the invention, multiple planar sections of wire mesh are spaced apart by suitable porous sheets of dielectric material. Successive wire mesh sections are alternately connected to one of two terminals. The resulting laminate assembly is supported within a fluid type cartridge which provides the cell fusion chamber.

BRIEF DESCRIPTION OF THE DRAWINGS

FIG. 2 is an enlarged, vertical sectional view of the first embodiment of my invention.

FIG. 3 is an enlarged, horizontal sectional view of the electrode spacer of my first embodiment.

FIG. 6 is a simplified, horizontal sectional view illustrating the electrode arrangement of the second embodiment of my invention.

DESCRIPTION OF THE PREFERRED EMBODIMENTS

Figure 1:
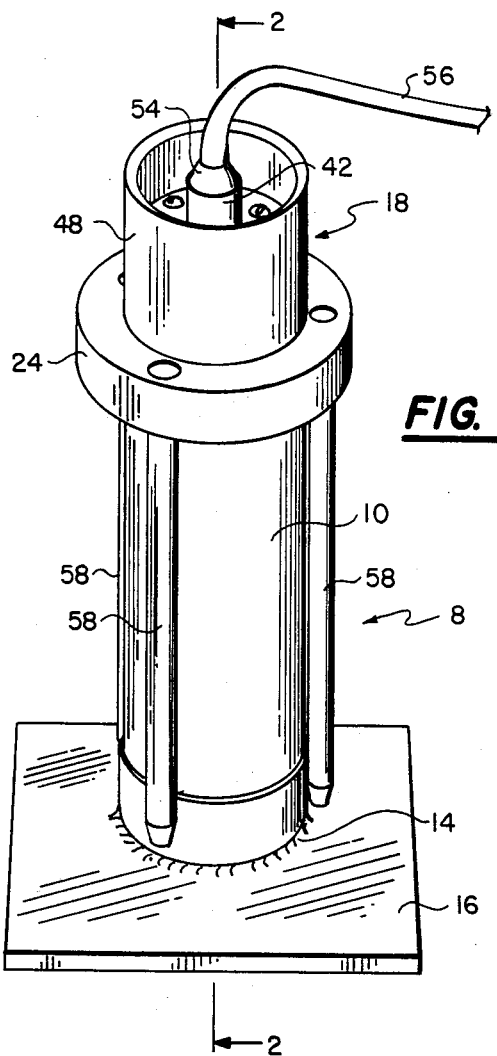
FIG. 1 is a perspective view of the first embodiment of my invention.

Referring to FIGS. 1 and 2, the first embodiment 8 of my invention includes a thick-walled cylinder 10 having a central, axially extending bore defining a cell fusion chamber 12. The cylinder 10 is preferably made of stainless steel and its lower end is secured by welding 14 to a base 16 in the form of a stainless steel plate. The volume of the chamber 12 is preferably approximately one milliliter. The thick walls of the stainless steel cylinder provide a vessel with a substantial amount of thermal inertia. This permits the cylinder to be cooled to a specific temperature which can be maintained with negligible fluctuation during the electro cell fusion process.

The first embodiment of my invention further includes a cap 18 (FIGS. 1 and 2) which supports the primary electrode 20 within the chamber and also seals the upper end of the chamber. The cap includes a cylindrical body portion 22 and a disk-shaped base portion 24. The base and body portions of the cap are preferably formed of a single piece of stainless steel. The upper end of the electrode 20 is rigidly fixed in and extends through a dielectric feedthrough member 26. This member is preferably made of TEFLON material. The enlarged end 26a of the feedthrough member is seated within the lower end of the cylindrical bore 28 in the body portion of the cap. The intermediate segment 26b of the feedthrough member snugly fits in a smaller bore 30 which extends through the base portion 24 of the cap and communicates with the bore 28. The lower end 26c of the feedthrough member extends below the base portion 24 of the cap and is adapted for insertion in the upper end of the chamber 12. It has four ribs spaced ninety degrees apart and its terminal end is tapered to facilitate insertion into the upper end of the chamber 12. Preferably, the upper end of the chamber diverges outwardly at 12a to facilitate guiding the lower end 26c of the feedthrough member into the chamber.

The lower portion of the positive electrode 20 extends through a dielectric spacer 32 (FIG. 2). This spacer is preferably made of TEFLON material. It has four ribs 34 (FIG. 3) spaced ninety degrees apart. Preferably, the upper and lower ends of the spacer 32 are tapered. In general, the configuration and dimensions of the spacer 32 are similar to the lower end 26c of the feedthrough member. The ribbed construction permits fluid to flow within the chamber 12 past the spacer. The distance between the ends of opposing ribs 34 is slightly smaller than the diameter of the chamber 12. Thus, the spacer 32 can be readily slid down the chamber 12 yet will firmly hold the primary electrode 20 in a central location within the chamber.

The underside of the base portion 24 of the cap is formed with an annular recess 36. This recess permits pressure relief from the chamber 12, between the ribs of the feedthrough member end 26c and into the recess.

Referring again to FIG. 2, a cover plate 38 extends across the upper end of the body portion of the cap and is secured thereto by screws 40. A BNC coaxial type female jack 42 is mounted to the cover plate 38. The jack 42 is grounded through the metal cover plate 38 to the cap 18 and the cylinder 10. The center terminal of the jack 42 is connected to the upper end of the primary electrode 20 through terminals 44 connected by wire 46. A protective shield 48 fits over the jack 42 and body portion 22 of the cap. The electrical connections within the shield are protected against moisture by sealing means in the form of a resilient, compressible O-ring 50. This O-ring seats within an angular groove 52 extending around the upper end of the body portion 22 of the cap. The shield 48 has a generally cylindrical configuration with an inside diameter slightly larger than the outside diameter of the body portion 22. When the shield is slid over the body portion, the O-ring 52 is squeezed against the inner wall of the shield to provide a fluid impervious seal. The O-ring thus holds the shield in position and prevents moisture from travelling up into the region of the jack between the shield and the body portion.

As is illustrated in FIG. 2, the shield 48 is open at its upper end to permit a coaxial plug 54 attached to coaxial cable 56 to be connected with the jack 42.

The first embodiment of my invention is provided with guide means to prevent the central electrode 20 from being bent or broken during insertion into the chamber 12. Specifically, three guide rods or pins 58 (FIGS. 1 and 2) extend vertically downward from the outer periphery of the base portion 24 of the cap. The pins 58 preferably have a round cross section and are also made of stainless steel. Their upper ends are rigidly secured within holes 60 (FIG. 2) formed at three locations spaced one-hundred and twenty degrees apart. The spacing between the guide pins 58 is such that the cylinder 10 will fit therebetween with each of the guide pins spaced closely to the other wall of the cylinder as illustrated in FIG. 2. The upper end of the cylinder 10 is tapered at 10a and the lower ends of the guide pins 58 are tapered at 58a. This makes the guide pins easy to manually slide over the upper end of the cylinder 10. The guide pins 58 extend sufficiently below the lower end of the electrode 20 so that the lower end of the electrode will not be contacted by the upper end of the cylinder in any manner as the guide pins are inserted over the upper end of the cylinder. Also, the precise alignment of the guide pins positively positions the electrode 20 in the center of the chamber 12 and prevents the lower end of the electrode from contacting the walls of the chamber.

It is important that the electrode 20 have a particular cross-section. Cells in a fluid medium, when exposed to electric fields, generally behave like uncharged particles suspended in a liquid. The field induces charge separation in the cells. If the electric field is homogeneous, the cells will stay in place. However, if the electric field is inhomogeneous, such as that generated by electrodes with edges or a small radius, then the force of the electric field on the sides of the cells closer to the field concentration point is larger than the force on the opposite side of the cells. The result is that the cells move towards the field concentration area. Accordingly, an alternating (AC) electric field can be used to move the cells in one direction. When the cells come closer to the area of field concentration, they start being attracted to each other and form pearl chains of two or more cells.

Because of the foregoing, the electrode 20 (FIG. 2) preferably has a round cross-section. In the first embodiment of my invention, the electrode 20 preferably has a diameter of approximately 0.025 inches and the chamber 12 has a diameter of approximately 0.180 inches.

The heavy, stainless steel construction of the first embodiment of my invention gives the apparatus high durability. This construction also makes the apparatus well suited to repeated sterilization.

Figure 5:
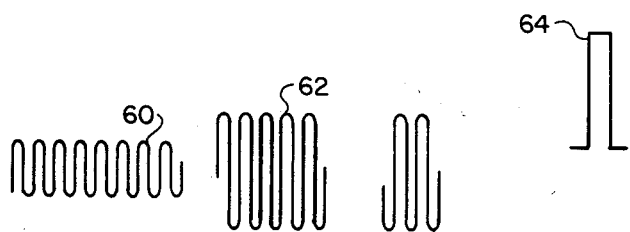
FIG. 5 is a sequence of electrical signal waveforms produced by the signal generator of FIG. 4.
Figure 4:
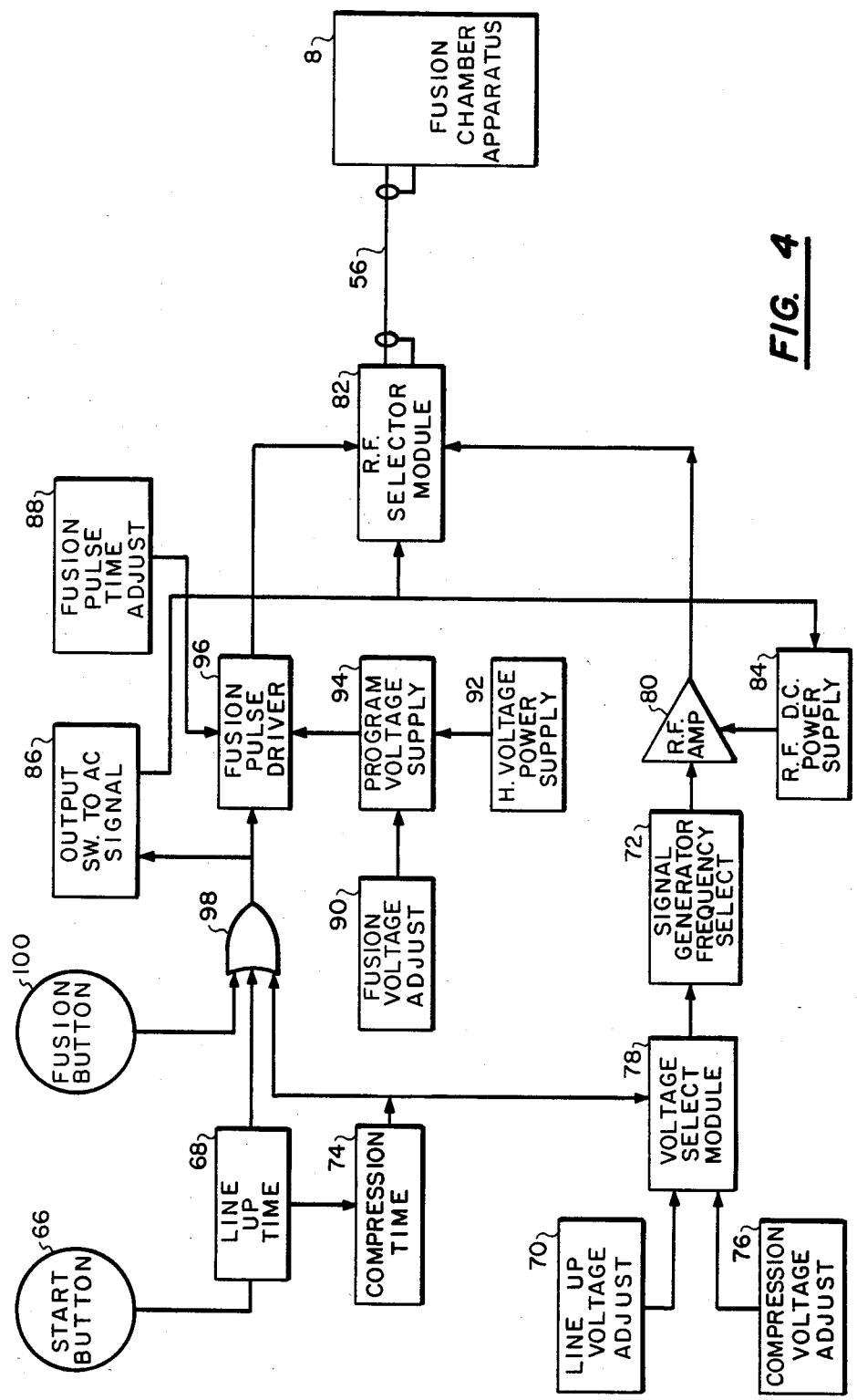
FIG. 4 is a block diagram of the signal generator used with the first embodiment of my invention.

FIG. 4 is a functional block diagram of a signal generator which may be used with the first embodiment of my cell fusion apparatus illustrated in FIGS. 1 and 2. It can provide a train of three different successive waveforms used to accomplish the electro cell fusion process. Referring the FIG. 5, these waveforms include a line-up pulse 60, a compression pulse 62 and a fusion pulse 64. These waveform names refer to the common procedures in electro cell fusion of first lining up the cells in chains, then compressing the cells for easier fusion and then fusing the cells with the final high voltage pulse. The parameter range of each of the pulse types is as follows. The first pulse train or line-up pulses have a sine wave, saw tooth or rectangular waveshape. The frequency is in the range of 20 KHz to 20 MHz. The field is in the range of 100–500 V/cm. The duration is typically 1–60 seconds. The second pulse train or compression pulses have a sine wave, saw tooth or rectangular waveshape. The frequency and amplitude ranges are the same as that of the first pulse train. The duration for the second pulse train is 1–10 seconds. The third pulse or fusion pulse has a rectangular waveshape. The frequency is a single pulse. The field is 1–7 kV/cm. The pulse width is 5–50 microseconds. The signal generator illustrated in FIG. 4 allows the parameters for each pulse train to be established and allows the pulse trains to be applied individually under manual control, or preprogrammed and applied automatically in succession. Referring to FIG. 4, the signal generator is activated by depressing start button 66. The duration of the line-up or first pulse train 60 is set by manually adjustable circuit 68. The amplitude of the first pulse train is set by manually adjustable circuit 70. The frequency of the first pulse train is set by manually adjustable signal generator circuit 72. Similarly, the duration of the second pulse train or compression pulse 62 is set by manually adjustable circuit 74. The amplitude of the second pulse train is set by manually adjustable circuit 76. The frequency of the second pulse train is set by manually adjustable signal generator circuit 72. Circuits 68, 70, 74 and 76 feed through voltage select module 78 to control the signal generator circuit 72. The output of the signal generator 72 is fed through RF amplifier 80 to RF selector module 82. The RF amplifier is energized through RF DC power supply 84. Circuit 86 does not permit power supply 84 to operate at full power unless the pulse trains are being generated.

Referring still to FIG. 4, the duration and amplitude of the third pulse or fusion pulse 64 are set by manually adjustable circuits 88 and 90, respectively. In conjunction with high voltage power supply circuit 92 and program voltage supply 94, the circuits 90 and 88 control a fusion pulse driver circuit 96. The output of the fusion pulse driver circuit 96 is also fed to RF selector module 82. This module is a fast coaxial relay which switches between the RF amplifier 80 and the fusion driver circuit 96 in the sequential application of the pulse trains to the fusion chamber apparatus in FIGS. 1 and 2 connected thereto by coaxial cable 56. AND gate 98 permits preprogrammed, automatic sequential application of the first, second and third pulse trains. Subsequent fusion pulses may be applied to the cell suspension fluid medium by activating fusion pushbutton 100.

The coaxial electrode configuration of the first embodiment 8 produces a highly inhomogeneous field. The field strength close to the outer electrode which is the cylinder 10 is lower than the field strength close to the inner electro 20 by a factor of approximately eight. The conductivity of the cell suspension fluid or solution used in the chamber 12 should be low enough to result in a minimum resistance of approximately 500 ohms. This corresponds to a maximum conductivity of $10^{-4}$ 1/ohm cm. The frequencies selected for the line-up and compression pulses need to be far enough from rotation inducing frequencies. If no information is available from literature regarding particular cell lines, experimentation with a wide variety of frequencies is advisable.

For some cell lines, the voltage levels and pulse durations required to form pearl chains and then fuse the cells may generate excessive heat. This can reduce the percentage of viable hybrids below acceptable levels. This can be overcome with the first embodiment of my apparatus by immersing the apparatus illustrated in FIGS. 1 and 2 in an ice bath. Alternatively, mechanical refrigerating devices may be used in conjunction with the apparatus. Yet another alternative is to use a thermelectric cooling element which operates on the Peltier effect. I have found that high yields of viable hybrids can be obtained where the apparatus is cooled to temperatures close to zero degrees centigrade.

It should be understood that the basic principles of the first embodiment 8 of my electro cell fusion apparatus can be incorporated into a wide variety of configurations. These include various chambers in which electrodes are suspended in spaced apart configurations. For example, FIG. 6 illustrates a second embodiment 102 of my invention in which a plurality of wire-like electrodes 104 extend vertically within an elongated chamber (not illustrated). The ends of the electrodes 104 extend through corresponding holes spaced circumferentially about dielectric support rings such as 106. The electrodes 104 are equally radially spaced from a central primary electrode 108. In an alternate configuration, the primary electrode may be a metal cylinder surrounding the electrodes 104.

Figure 7:
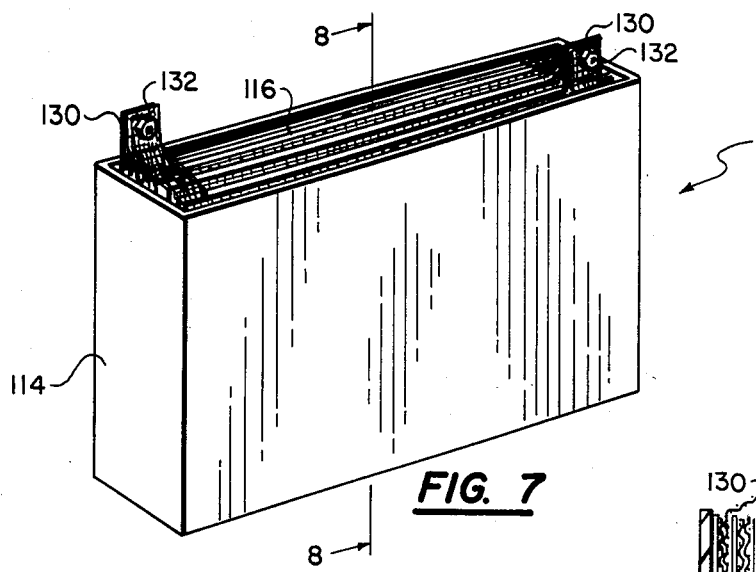
FIG. 7 is a perspective view of an electro cell fusion cartridge forming the third embodiment of my invention.
Figure 8:
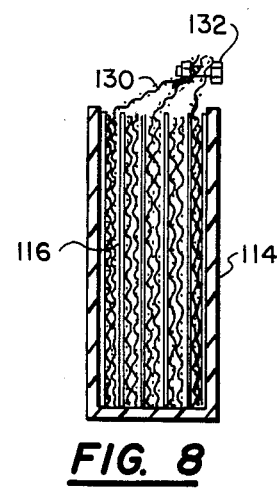
FIG. 8 is a vertical sectional view of the cartridge of FIG. 7.
Figure 9:
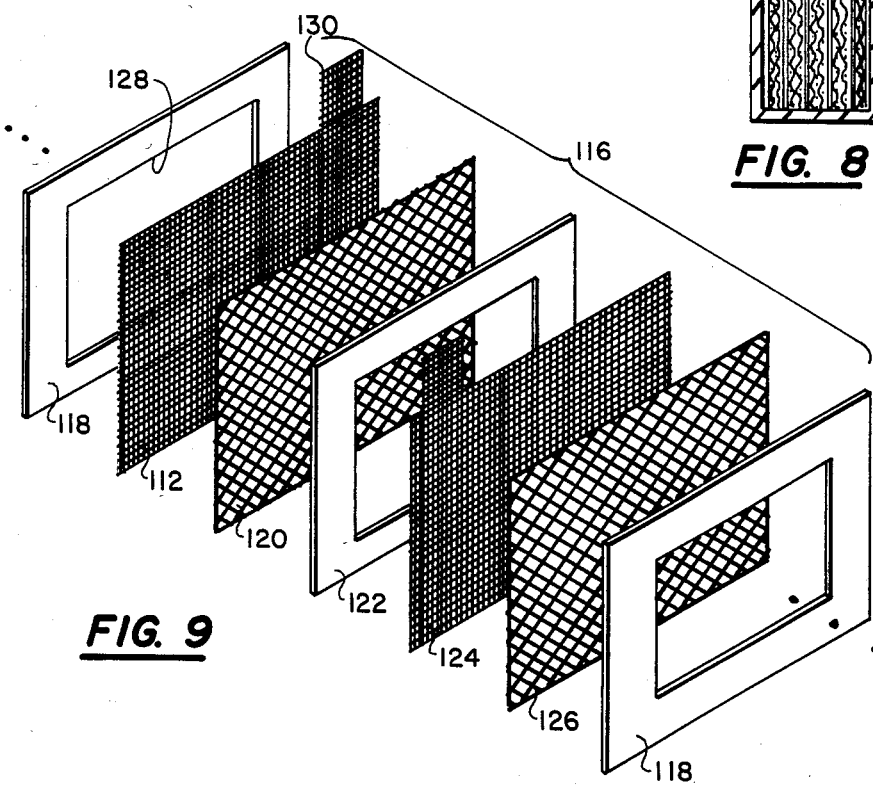
FIG. 9 is an exploded perspective view illustrating the laminate internal construction of the electro cell fusion cartridge of FIG. 7.

FIGS. 7–9 illustrate a third embodiment 110 of my invention in which stainless steel wire mesh electrodes such as 112 are spaced apart and mounted within a cell fusion chamber in the form of a rectangular cartridge 114. The laminate construction 116 (FIG. 8) within the cartridge 114 is illustrated in greater detail in FIG. 9. The laminate construction consists of a repeating sequence of spacer 118, wire mesh 112, insulative mesh 120, spacer 122, wire mesh 124, and insulative mesh 126. The pattern then repeats starting with spacer 118. This repeating sequence is indicated by the series of dots behind and in front of the succession of elements in FIG. 9. Each of the elements has a rectangular shaped outer boundary. Preferably, the length and width of the wire mesh elements is less than that of the spacer and insulative mesh elements to prevent the ends of adjacent wire mesh elements from contacting each other. Each of the spacer elements is preferably made of insulative, inert plastic material such as that sold under the trademark MYLAR. These spacers have a central cut-out region 128 to allow fluid to pass therethrough. Successive ones of the wire mesh elements have tabs 130 on opposite ends thereof as illustrated in FIG. 9. The tabs at opposite ends of the cartridge may then be connected together by bolt and nut combinations 132 (FIGS. 7 and 8) or other means to provide terminals for the signal generator leads. The insulative wire mesh elements such as 120 and 126 are preferably made of TEFLON material. The gauge of the stainless steel wire in the elements 112 and 124 is preferably 0.020 inches. The insulative mesh elements may have a similar gauge although the diameter of the individual strands thereof is not as important to the performance of the device as in the case of the wire mesh elements.

Having described preferred embodiments of my large volume electro cell fusion apparatus, it should be apparent to those skilled in the art that my invention may be modified in both arrangement and detail. For example, a laminate construction of wire mesh and insulative mesh spacers could be rolled into a cylindrical configuration and mounted within a cylindrical chamber housing. Therefore, the protection afforded my invention should only be limited in accordance with the scope of the following claims.

I claim:

1. An electro cell fusion apparatus comprising:
   a metal vessel forming a first electrode and having an elongate cylindrical chamber formed therein and opening at an upper end of the vessel;
   an elongate wire having a round cross-section forming a second electrode;
   cap means connected to an end of the second electrode and configured to removably mate with the upper end of the vessel for positioning the second electrode so that it extends concentrically within the cylindrical chamber; and
   means for sequentially generating and applying predetermined alternating electric currents and unidirectional current pulses to the first and second electrodes so that when a plurality of live cells are supported in a quantity of fluid medium contained in the chamber the cells will undergo dielectrophoresis and dielectric breakdown thereby causing adjacent cells to fuse and produce viable hybrids.

2. An apparatus according to claim 1 and further comprising means for guiding the cap over the upper end of the vessel to prevent the second electrode from contacting the first electrode.

3. An apparatus according to claim 2 wherein the vessel is cylindrical and the guiding means includes a plurality of guide rods extending from spaced locations about a periphery of the cap means.

4. An apparatus according to claim 1 and further comprising an electrically insulative spacer element surrounding the wire between the ends thereof and dimensioned to contact an interior wall of the chamber to concentrically position the wire therein.

5. An apparatus according to claim 1 wherein the chamber has a volume of approximately one milliliter.

6. An apparatus according to claim 1 and further comprising a base attached to and supporting the vessel.

7. An apparatus according to claim 1 wherein the vessel is made of stainless steel.

8. An apparatus according to claim 1 wherein the cap means includes a metal body portion having a central bore therethrough and a dielectric member surrounding and holding the end of the wire and positioned in the bore so that the wire extends therethrough.

9. An apparatus according to claim 1 wherein means for generating and applying the currents to the electrodes includes a coaxial connector mounted on the cap means.

10. An apparatus according to claim 1 wherein the means for generating and applying the currents includes an adjustable signal generator.

11. An electro cell fusion apparatus comprising:
    a vessel having an elongate chamber formed therein;
    a first elongate electrode having a round cross-section;
    means for supporting the first electrode so that it extends longitudinally within the chamber;
    a plurality of elongate second electrodes;
    means for supporting the second electrodes so that they extend longitudinally within the chamber spaced circumferentially about the first electrode equal radial distances therefrom;
    means for sequentially generating and applying predetermined alternating electric currents and unidirectional current pulses to the first and second electrodes so that when a plurality of live cells are supported in a quantity of fluid medium contained in the chamber the cells will undergo dielectrophoresis and dielectric breakdown thereby causing adjacent cells to fuse and produce viable hybrids.

12. An electro cell fusion apparatus comprising:
    a metal vessel forming a first electrode and having an elongate cylindrical chamber formed therein;
    a plurality of elongate second electrodes;
    means for supporting the second electrodes so that they extend longitudinally within the chamber and are arranged in a symmetric ring configuration equally spaced a first distance from each other and equally spaced a second distance from an inner wall of the chamber; and
    means for sequentially generating and applying predetermined alternating electric currents and unidirectional current pulses to the first and second electrodes so that when a plurality of live cells are supported in a quantity of fluid medium contained in the chamber the cells will undergo dielectrophoresis and dielectric breakdown thereby causing adjacent cells to fuse and produce viable hybrids.

13. An electro cell fusion apparatus comprising:
    a vessel having an interior chamber;
    first and second wire mesh electrodes closely positioned in the chamber;
    an insulative wire mesh element spaced between the first and second electrodes; and
    means for sequentially generating and applying predetermined alternating electric currents and unidirectional current pulses to the first and second electrodes so that when a plurality of live cells are supported in a quantity of fluid medium contained in the chamber the cells will undergo dielectrophoresis and dielectric breakdown thereby causing adjacent cells to fuse and produce viable hybrids.

* * * * *